US009402679B2

(12) United States Patent
Ginnebaugh et al.

(10) Patent No.: US 9,402,679 B2
(45) Date of Patent: Aug. 2, 2016

(54) SURGICAL INSTRUMENT AND METHOD

(75) Inventors: Fred Ginnebaugh, Sunnyvale, CA (US);
Ryan Abbott, San Jose, CA (US); Justin Williams, San Jose, CA (US); Kenny Dang, San Jose, CA (US); Rohit Girotra, San Francisco, CA (US)

(73) Assignee: MAQUET Cardiovascular LLC, San Jose, CA (US)

( * ) Notice: Subject to any disclaimer, the term of this patent is extended or adjusted under 35 U.S.C. 154(b) by 1026 days.

(21) Appl. No.: 12/472,657

(22) Filed: May 27, 2009

(65) Prior Publication Data
US 2009/0299367 A1    Dec. 3, 2009

Related U.S. Application Data

(60) Provisional application No. 61/056,207, filed on May 27, 2008.

(51) Int. Cl.
A61B 18/14    (2006.01)
A61B 18/08    (2006.01)
A61B 18/00    (2006.01)

(52) U.S. Cl.
CPC ............ *A61B 18/085* (2013.01); *A61B 18/1445* (2013.01); *A61B 2018/0063* (2013.01); *A61B 2018/00345* (2013.01); *A61B 2018/00404* (2013.01); *A61B 2018/00601* (2013.01); *A61B 2018/00916* (2013.01)

(58) Field of Classification Search
CPC ............ A61B 18/085; A61B 18/1445; A61B 2018/1452
USPC .............. 606/27–29, 37, 52, 207; 607/98, 99, 607/115
See application file for complete search history.

(56) References Cited

U.S. PATENT DOCUMENTS

| | | |
|---|---|---|
| 2,137,710 A | 12/1937 | Anderson |
| 4,031,898 A | 6/1977 | Hiltebrandt et al. |
| 4,071,028 A | 1/1978 | Perkins |
| 4,128,099 A | 12/1978 | Bauer |
| 4,281,646 A | 8/1981 | Kinoshita |
| 4,418,692 A | 12/1983 | Guay |
| 4,468,217 A | 8/1984 | Kuzmick et al. |
| 4,759,362 A | 7/1988 | Taniguchi |

(Continued)

FOREIGN PATENT DOCUMENTS

| | | |
|---|---|---|
| EP | 1330991 A1 | 7/2003 |
| EP | 1632192 A1 | 3/2006 |

(Continued)

OTHER PUBLICATIONS

International Search Report and Written Opinion dated Jan. 19, 2010 for PCT Application No. PCT/US2009/045272.

*Primary Examiner* — Michael Peffley
*Assistant Examiner* — Thomas Giuliani

(57) ABSTRACT

A surgical instrument includes an elongated body having a distal end, a proximal end, and a bore extending between the distal and proximal ends, a pair of jaws for severing vessel mounted on the distal end of the body, wherein at least one of the jaws has an electrically conductive material, and a handle coupled to the proximal end of the elongated body, wherein in a first mode of operation, the electrically conductive material is for receiving energy from a DC source, and in a second mode of operation, the electrically conductive material is for receiving energy from a RF source.

39 Claims, 13 Drawing Sheets

(56) References Cited

U.S. PATENT DOCUMENTS

| | | | |
|---|---|---|---|
| 4,767,519 A | 8/1988 | de Nora | |
| 4,801,015 A | 1/1989 | Lubock et al. | |
| 4,884,559 A | 12/1989 | Collins | |
| 5,009,661 A | 4/1991 | Michelson | |
| 5,052,402 A | 10/1991 | Bencini et al. | |
| 5,098,430 A | 3/1992 | Fleenor | |
| 5,108,474 A | 4/1992 | Riedy et al. | |
| 5,147,356 A | 9/1992 | Bhatta | |
| 5,151,102 A | 9/1992 | Kamiyama et al. | |
| 5,154,709 A | 10/1992 | Johnson | |
| 5,156,613 A | 10/1992 | Sawyer | |
| 5,160,334 A | 11/1992 | Billings et al. | |
| 5,217,460 A | 6/1993 | Knoepfler | |
| 5,258,006 A | 11/1993 | Rydell et al. | |
| 5,282,799 A | 2/1994 | Rydell | |
| 5,290,278 A | 3/1994 | Anderson | |
| 5,300,065 A | 4/1994 | Anderson | |
| 5,312,426 A | 5/1994 | Segawa et al. | |
| 5,314,424 A | 5/1994 | Nicholas | |
| 5,318,040 A | 6/1994 | Kensey et al. | |
| 5,336,221 A | 8/1994 | Anderson | |
| 5,342,381 A | 8/1994 | Tidemand | |
| 5,352,222 A | 10/1994 | Rydell | |
| 5,356,408 A | 10/1994 | Rydell | |
| 5,361,583 A | 11/1994 | Huitema | |
| 5,364,395 A * | 11/1994 | West, Jr. | 606/46 |
| 5,383,888 A | 1/1995 | Zvenyatsky et al. | |
| 5,405,344 A | 4/1995 | Williamson et al. | |
| 5,443,463 A | 8/1995 | Stern et al. | |
| 5,445,638 A | 8/1995 | Rydell et al. | |
| 5,451,222 A | 9/1995 | De Maagd et al. | |
| 5,453,599 A | 9/1995 | Hall, Jr. | |
| 5,462,546 A | 10/1995 | Rydell | |
| 5,472,442 A | 12/1995 | Klicek | |
| 5,496,317 A | 3/1996 | Goble et al. | |
| 5,507,744 A | 4/1996 | Tay et al. | |
| 5,507,773 A | 4/1996 | Huitema et al. | |
| 5,509,922 A | 4/1996 | Aranyi et al. | |
| 5,514,134 A | 5/1996 | Rydell et al. | |
| 5,562,503 A | 10/1996 | Eliman et al. | |
| 5,599,350 A | 2/1997 | Schulze et al. | |
| 5,624,452 A | 4/1997 | Yates | |
| 5,647,871 A | 7/1997 | Levine et al. | |
| 5,669,934 A | 9/1997 | Sawyer | |
| 5,674,219 A | 10/1997 | Monson et al. | |
| 5,683,412 A | 11/1997 | Scarfone | |
| 5,709,675 A | 1/1998 | Williams | |
| 5,709,680 A | 1/1998 | Yates et al. | |
| 5,716,366 A | 2/1998 | Yates | |
| 5,722,962 A | 3/1998 | Garcia | |
| 5,741,285 A | 4/1998 | McBrayer et al. | |
| 5,752,973 A | 5/1998 | Kieturakis | |
| 5,755,717 A * | 5/1998 | Yates et al. | 606/51 |
| 5,766,134 A | 6/1998 | Lisak et al. | |
| 5,766,166 A | 6/1998 | Hooven | |
| 5,776,130 A | 7/1998 | Buysse et al. | |
| 5,807,393 A | 9/1998 | Williamson et al. | |
| 5,810,810 A | 9/1998 | Tay et al. | |
| 5,827,271 A | 10/1998 | Buysse et al. | |
| 5,833,690 A | 11/1998 | Yates et al. | |
| 5,843,017 A | 12/1998 | Yoon | |
| 5,849,011 A | 12/1998 | Jones et al. | |
| 5,853,410 A | 12/1998 | Greff et al. | |
| 5,860,975 A | 1/1999 | Goble et al. | |
| 5,871,496 A | 2/1999 | Ginn et al. | |
| 5,891,141 A | 4/1999 | Rydell | |
| 5,906,630 A | 5/1999 | Anderhub et al. | |
| 5,908,420 A | 6/1999 | Parins et al. | |
| 5,911,719 A | 6/1999 | Eggers | |
| 5,944,718 A | 8/1999 | Austin et al. | |
| 5,947,984 A | 9/1999 | Whipple | |
| 5,954,686 A | 9/1999 | Garito et al. | |
| 5,997,533 A | 12/1999 | Kuhns | |
| 6,004,320 A | 12/1999 | Casscells et al. | |
| 6,022,313 A | 2/2000 | Ginn et al. | |
| 6,024,741 A | 2/2000 | Williamson et al. | |
| 6,027,501 A | 2/2000 | Goble et al. | |
| 6,033,424 A | 3/2000 | Ouchi | |
| 6,039,733 A | 3/2000 | Buysse et al. | |
| 6,059,781 A | 5/2000 | Yamanashi et al. | |
| 6,066,151 A | 5/2000 | Miyawaki et al. | |
| 6,074,389 A | 6/2000 | Levine et al. | |
| 6,110,190 A | 8/2000 | Ginn et al. | |
| 6,113,596 A | 9/2000 | Hooven et al. | |
| 6,174,309 B1 | 1/2001 | Wrublewski et al. | |
| 6,179,837 B1 | 1/2001 | Hooven | |
| 6,190,386 B1 | 2/2001 | Rydell | |
| 6,206,876 B1 | 3/2001 | Levine et al. | |
| 6,254,623 B1 | 7/2001 | Haibel et al. | |
| 6,267,761 B1 | 7/2001 | Ryan | |
| 6,270,497 B1 | 8/2001 | Sekino et al. | |
| 6,273,887 B1 | 8/2001 | Yamauchi et al. | |
| 6,352,503 B1 | 3/2002 | Matsui et al. | |
| 6,352,532 B1 | 3/2002 | Kramer et al. | |
| 6,391,029 B1 | 5/2002 | Hooven et al. | |
| 6,406,454 B1 | 6/2002 | Hajianpour | |
| 6,432,105 B1 | 8/2002 | Ellman et al. | |
| 6,458,122 B1 | 10/2002 | Pozzato | |
| 6,464,701 B1 | 10/2002 | Hooven et al. | |
| 6,478,794 B1 | 11/2002 | Trapp et al. | |
| 6,517,536 B2 | 2/2003 | Hooven et al. | |
| 6,524,307 B1 | 2/2003 | Palmerton et al. | |
| 6,527,771 B1 | 3/2003 | Weadock et al. | |
| 6,544,210 B1 | 4/2003 | Trudel et al. | |
| 6,551,313 B1 | 4/2003 | Levin | |
| 6,576,033 B1 | 6/2003 | Booth | |
| 6,582,451 B1 | 6/2003 | Marucci et al. | |
| 6,582,582 B2 | 6/2003 | Becking | |
| 6,602,252 B2 | 8/2003 | Mollenauer | |
| 6,613,069 B2 | 9/2003 | Boyd et al. | |
| 6,626,901 B1 | 9/2003 | Treat et al. | |
| 6,652,514 B2 | 11/2003 | Eliman et al. | |
| 6,656,177 B2 | 12/2003 | Truckai et al. | |
| 6,663,610 B1 | 12/2003 | Thompson et al. | |
| 6,682,528 B2 | 1/2004 | Frazier et al. | |
| 6,685,665 B2 | 2/2004 | Booth et al. | |
| 6,695,837 B2 | 2/2004 | Howell | |
| 6,746,504 B2 | 6/2004 | Booth | |
| 6,770,072 B1 | 8/2004 | Truckai et al. | |
| 6,773,409 B2 | 8/2004 | Truckai et al. | |
| 6,802,843 B2 | 10/2004 | Truckai et al. | |
| 6,821,273 B2 | 11/2004 | Mollenauer | |
| 6,830,569 B2 | 12/2004 | Thompson et al. | |
| 6,860,880 B2 | 3/2005 | Treat et al. | |
| 6,908,463 B2 | 6/2005 | Treat et al. | |
| 6,958,070 B2 | 10/2005 | Witt et al. | |
| 6,966,907 B2 | 11/2005 | Goble | |
| 6,966,909 B2 | 11/2005 | Marshall et al. | |
| 6,994,707 B2 * | 2/2006 | Ellman et al. | 606/42 |
| 7,033,356 B2 | 4/2006 | Latterell et al. | |
| 7,094,231 B1 | 8/2006 | Eliman et al. | |
| 7,112,199 B2 | 9/2006 | Cosmescu | |
| 7,147,637 B2 | 12/2006 | Goble | |
| 7,204,835 B2 | 4/2007 | Latterell et al. | |
| 7,211,080 B2 | 5/2007 | Treat et al. | |
| 7,316,683 B2 | 1/2008 | Kasahara et al. | |
| 7,326,202 B2 | 2/2008 | McGaffigan | |
| 7,329,257 B2 | 2/2008 | Kanehira et al. | |
| 7,364,577 B2 | 4/2008 | Wham et al. | |
| 7,367,976 B2 | 5/2008 | Lawes et al. | |
| 7,396,356 B2 | 7/2008 | Mollenauer | |
| 7,513,896 B2 | 4/2009 | Orszulak | |
| 7,632,270 B2 * | 12/2009 | Livneh | 606/51 |
| 7,645,289 B2 | 1/2010 | Bayer | |
| 7,695,470 B1 | 4/2010 | Stewart et al. | |
| 7,699,861 B2 | 4/2010 | Bayer | |
| 7,887,558 B2 | 2/2011 | Lin et al. | |
| 7,918,845 B2 | 4/2011 | Saadat et al. | |
| 7,918,848 B2 | 4/2011 | Lau et al. | |
| 8,197,472 B2 | 6/2012 | Lau et al. | |
| 8,221,306 B2 | 7/2012 | Okada et al. | |
| 8,251,989 B1 | 8/2012 | Newton et al. | |
| 8,257,352 B2 | 9/2012 | Lawes et al. | |
| 8,425,508 B2 | 4/2013 | Kasahara et al. | |

(56) References Cited

U.S. PATENT DOCUMENTS

| | | |
|---|---|---|
| 8,657,818 B2 | 2/2014 | Lin |
| 2002/0019631 A1 | 2/2002 | Kidder et al. |
| 2002/0058938 A1 | 5/2002 | Cosmescu |
| 2002/0115997 A1 | 8/2002 | Truckai et al. |
| 2002/0128603 A1 | 9/2002 | Booth et al. |
| 2003/0014052 A1 | 1/2003 | Buysse et al. |
| 2003/0060816 A1* | 3/2003 | Iida .................. 606/29 |
| 2003/0073991 A1 | 4/2003 | Francischelli |
| 2003/0125734 A1 | 7/2003 | Mollenauer |
| 2003/0130654 A1 | 7/2003 | Kasahara et al. |
| 2003/0130674 A1 | 7/2003 | Kasahara et al. |
| 2003/0130675 A1 | 7/2003 | Kasahara et al. |
| 2003/0139649 A1 | 7/2003 | Kasahara et al. |
| 2003/0144652 A1 | 7/2003 | Baker et al. |
| 2003/0144660 A1 | 7/2003 | Mollenauer |
| 2003/0163123 A1 | 8/2003 | Goble et al. |
| 2003/0171747 A1 | 9/2003 | Kanehira et al. |
| 2003/0187429 A1 | 10/2003 | Karasawa et al. |
| 2004/0054365 A1 | 3/2004 | Goble |
| 2004/0064151 A1 | 4/2004 | Mollenauer |
| 2004/0078035 A1 | 4/2004 | Kanehira et al. |
| 2004/0102450 A1 | 5/2004 | Ewing et al. |
| 2004/0133228 A1 | 7/2004 | Bayer |
| 2004/0176756 A1 | 9/2004 | McGaffigan |
| 2004/0204725 A1 | 10/2004 | Bayer |
| 2004/0260279 A1 | 12/2004 | Goble et al. |
| 2005/0033278 A1 | 2/2005 | McClurken et al. |
| 2005/0049633 A1 | 3/2005 | Watanabe |
| 2005/0072827 A1 | 4/2005 | Mollenauer |
| 2005/0113826 A1 | 5/2005 | Johnson et al. |
| 2005/0171533 A1 | 8/2005 | Latterell et al. |
| 2006/0074444 A1 | 4/2006 | Lin et al. |
| 2006/0211916 A1 | 9/2006 | Kasahara et al. |
| 2006/0217697 A1 | 9/2006 | Lau et al. |
| 2006/0217706 A1* | 9/2006 | Lau et al. .................. 606/45 |
| 2006/0235379 A1* | 10/2006 | McClurken et al. ......... 606/45 |
| 2006/0271037 A1 | 11/2006 | Maroney et al. |
| 2007/0021405 A1 | 1/2007 | Abouabdellah et al. |
| 2007/0021424 A1 | 1/2007 | Abouabdellah et al. |
| 2007/0027141 A1 | 2/2007 | Abouabdellah et al. |
| 2007/0078456 A1 | 4/2007 | Dumbauld et al. |
| 2007/0149993 A1 | 6/2007 | Kasahara et al. |
| 2007/0213749 A1 | 9/2007 | Kogasaka et al. |
| 2007/0260242 A1 | 11/2007 | Dycus et al. |
| 2007/0293856 A1 | 12/2007 | Paul et al. |
| 2007/0293858 A1 | 12/2007 | Fischer |
| 2008/0015567 A1* | 1/2008 | Kimura .................. 606/41 |
| 2008/0015575 A1* | 1/2008 | Odom et al. ............... 606/51 |
| 2008/0039835 A1 | 2/2008 | Johnson et al. |
| 2008/0154091 A1 | 6/2008 | Dejima et al. |
| 2008/0306335 A1 | 12/2008 | Lau et al. |
| 2009/0024121 A1 | 1/2009 | Kasahara et al. |
| 2009/0118730 A1 | 5/2009 | Mollenauer |
| 2009/0299367 A1 | 12/2009 | Ginnebaugh et al. |
| 2010/0048992 A1 | 2/2010 | Okada et al. |
| 2010/0292533 A1 | 11/2010 | Kasahara et al. |
| 2011/0046439 A1 | 2/2011 | Pamnani et al. |
| 2011/0046624 A1 | 2/2011 | Lin |
| 2011/0257643 A1 | 10/2011 | Lau et al. |
| 2011/0288369 A1 | 11/2011 | Ginnebaugh et al. |
| 2011/0288546 A1 | 11/2011 | Abbott et al. |

FOREIGN PATENT DOCUMENTS

| | | |
|---|---|---|
| EP | 1878399 A2 | 1/2008 |
| EP | 1894535 A1 | 3/2008 |
| WO | 2005048863 A1 | 6/2005 |
| WO | 2009039179 A1 | 3/2009 |

* cited by examiner

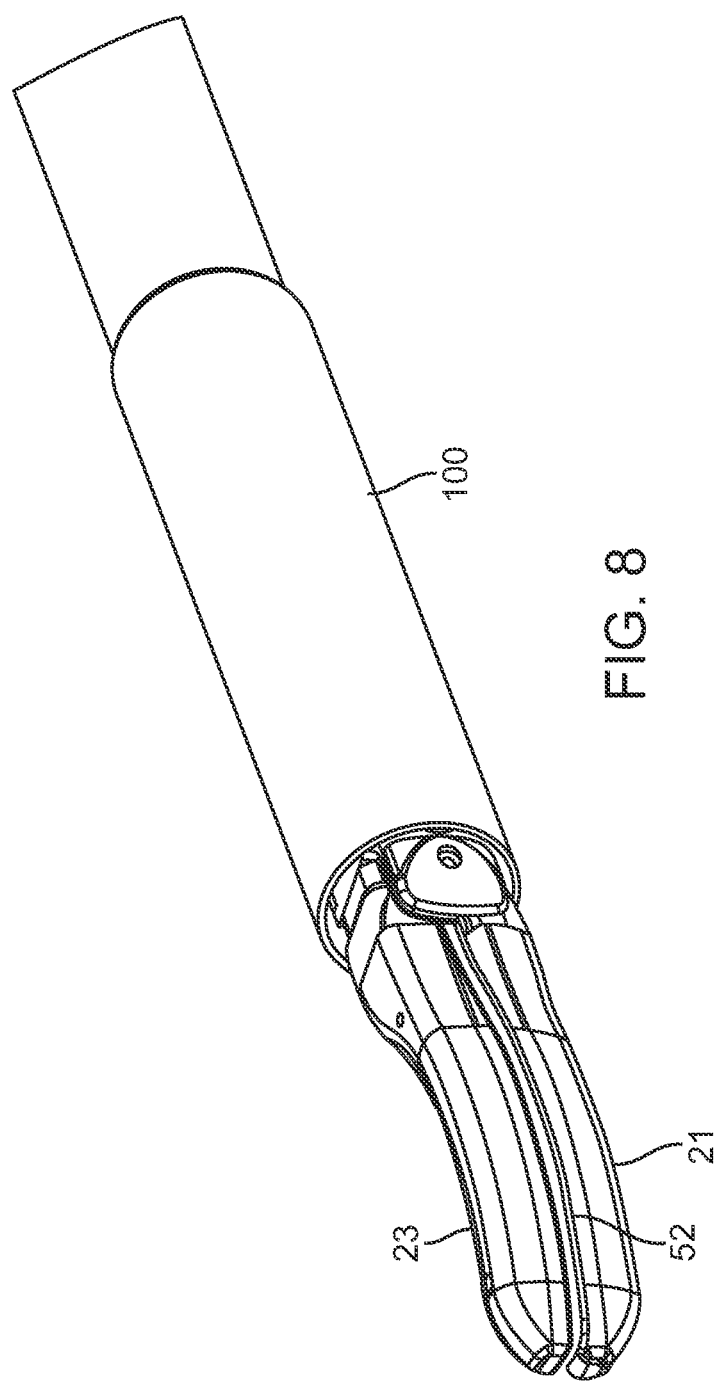

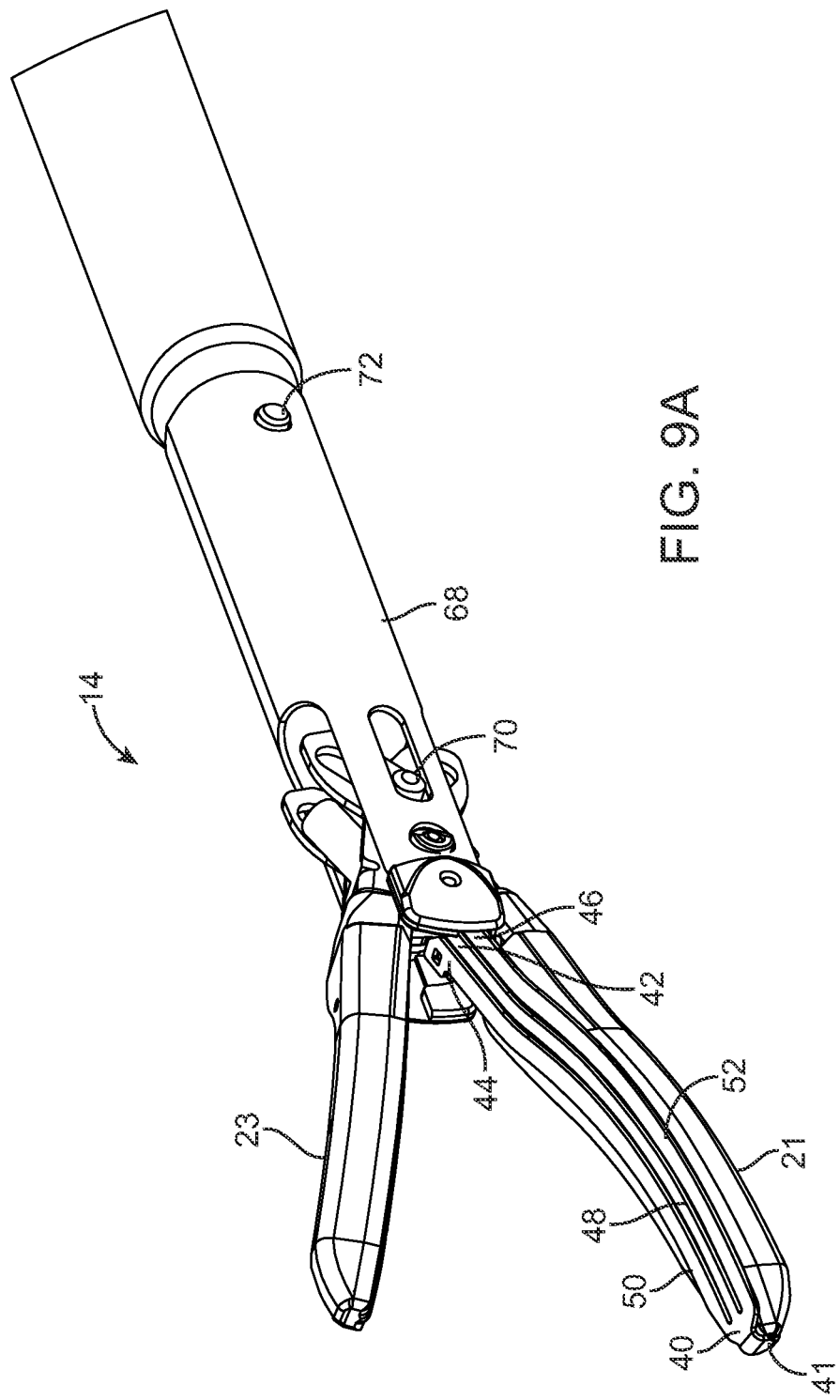

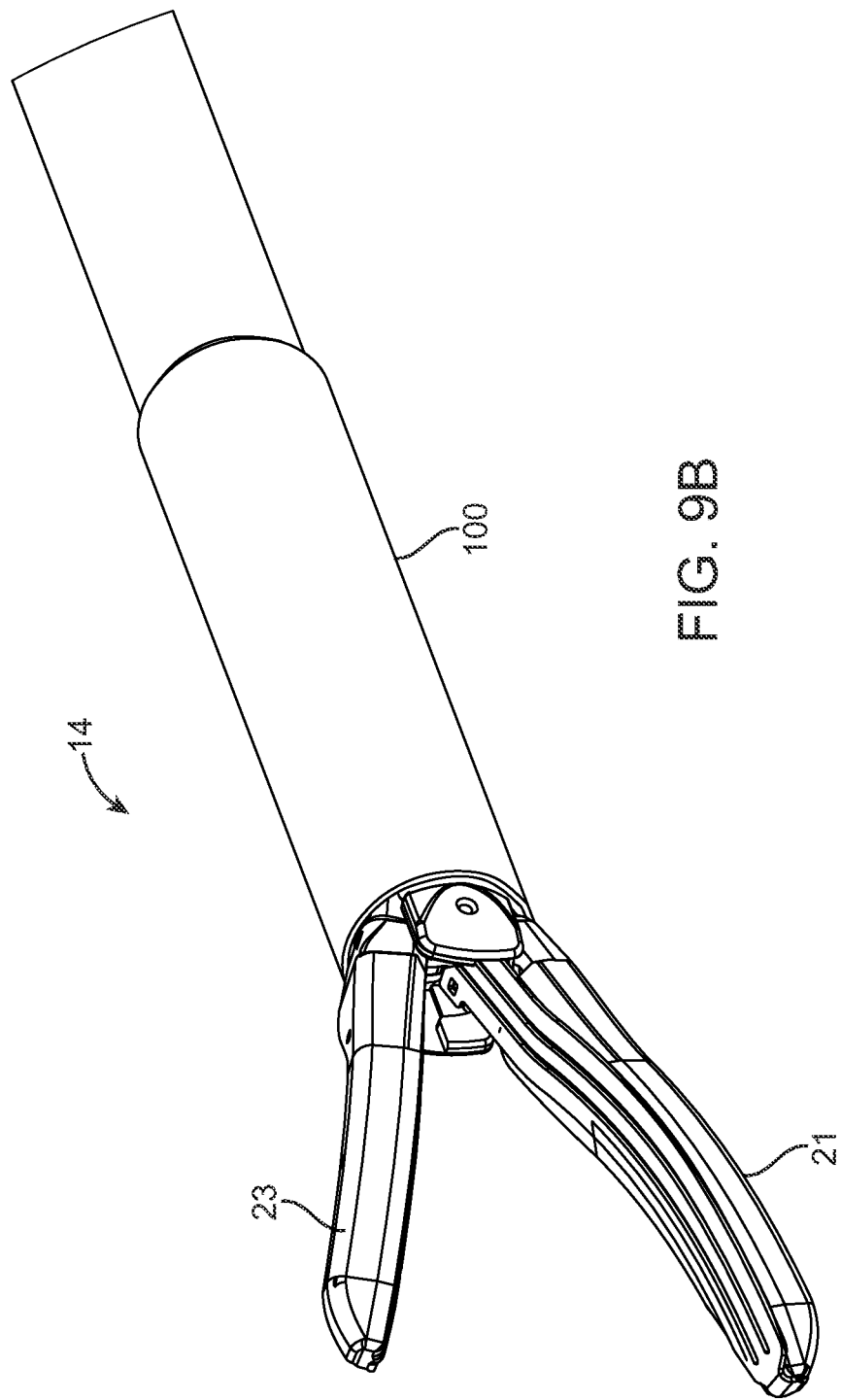

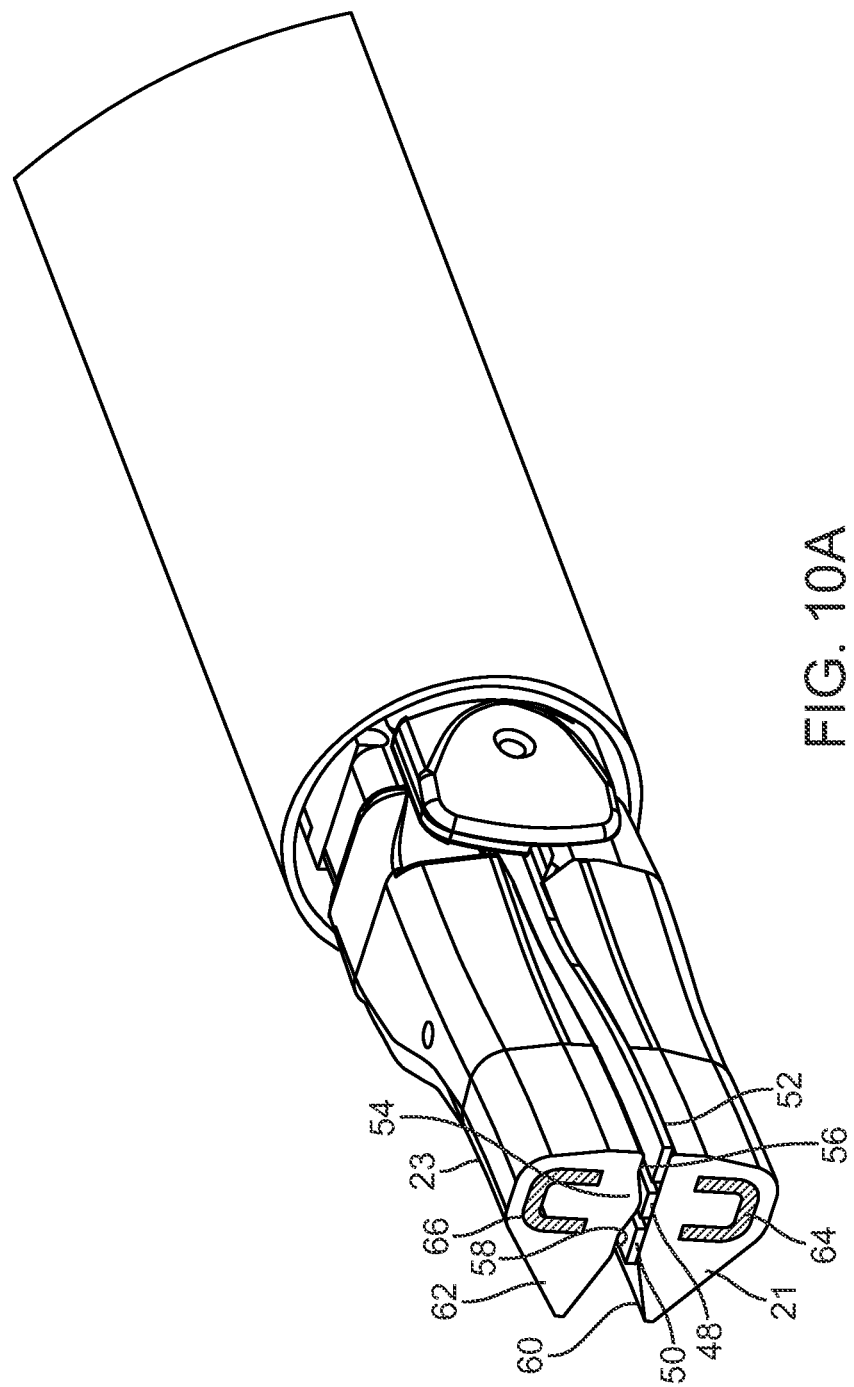

SURGICAL INSTRUMENT AND METHOD

RELATED APPLICATION DATA

This application claims priority to, and the benefit of, U.S. Provisional Application Ser. No. 61/056,207, filed on May 27, 2008, the entire disclosure of which is expressly incorporated by reference herein.

FIELD

This application relates to a surgical instrument for controlling bleeding at a surgical site, and more particularly, to a vessel harvesting device that includes a bleeding control feature.

BACKGROUND

In endoscopic vessel harvesting (EVH) surgical procedures, a long slender surgical instrument may be advanced into a tunnel next to the saphenous vein in a patient's leg, and along the saphenous vein to dissect the vessel away from adjacent tissue, and to sever side-branch vessels along the course of the vessel to be harvested. Similar technique may also be used to harvest a radial artery.

During the EVH procedure, vasculature in tunnel will occasionally bleed. This is a challenge for the individual performing the EVH procedure as well as for the patient. This is because blood may impair visualization of the target site during the procedure, and may cause wound complications for the patient. Existing instruments that perform EVH procedure do not provide bleeding control function to control bleeding at the tunnel. This is because the vessel harvesting instrument needs to have a low profile. Thus, providing an additional energy delivery feature in such instrument for controlling bleeding in the tunnel, which will increase the size of the instrument, is generally not desirable. Also, delivery of monopolar RF energy is not desirable for protecting a vessel. Thus, use of monopolar RF energy for bleeding control in a vessel harvesting procedure has been avoided.

SUMMARY

In accordance with some embodiments, a surgical instrument includes an elongated body having a distal end, a proximal end, and a bore extending between the distal and proximal ends, a surgical device including electrically conductive material mounted on the distal end of the body, a handle coupled to the proximal end of the elongated body, the handle including a manual control moveably mounted thereon, linkage disposed within the bore, wherein the linkage couples the manual control to the surgical device, and is configured for actuating movement of the surgical device in response to manipulation of the manual control, and a contact region of electrically conductive material disposed at the handle, wherein the contact region is electrically connected to the surgical device; wherein in a first mode of operation, the electrically conductive material of the surgical device is configured to provide heat, and in a second mode of operation, the electrically conductive material of the surgical device is configured to provide radiofrequency (RF) energy. The two modes of operation may be performed at different times, or simultaneously.

In accordance with other embodiments, a surgical instrument includes an elongated body having a distal end, a proximal end, and a bore extending between the distal and proximal ends, a pair of jaws for severing vessel mounted on the distal end of the body, wherein at least one of the jaws has an electrically conductive material, and a handle coupled to the proximal end of the elongated body, wherein in a first mode of operation, the electrically conductive material is for receiving energy from a direct current (DC) source, and in a second mode of operation, the electrically conductive material is for receiving energy from a RF source.

In accordance with other embodiments, a method for controlling bleeding at a surgical site in a patient includes inserting a surgical device into the patient, the surgical device having an electrically conductive material, supplying energy from a DC source to the electrically conductive material for performing a medical procedure, and supplying energy from a RF source to the electrically conductive material for controlling bleeding at the surgical site. By means of non-limiting examples, such medical procedure may include cutting a tissue, sealing a tissue, and/or cauterizing a tissue. In some embodiments, the medical procedure includes controlling bleeding.

In accordance with other embodiments, a surgical instrument includes an elongated body having a distal end, a proximal end, and a bore extending between the distal and proximal ends, and a jaw assembly located at the distal end of the elongated body, the jaw assembly having an operative element for cutting a target tissue, wherein the jaw assembly has a protrusion for abutment against a critical tissue, and the protrusion is sized so that when the protrusion is abutted against the critical tissue, the operative element is automatically placed at a desired position relative to the target tissue. In some embodiments, the target tissue includes tissue at a side branch vessel. Also, in some embodiments, the critical tissue includes tissue at a main branch vessel.

In accordance with other embodiments, a surgical instrument includes an elongated body having a distal end, a proximal end, and a bore extending between the distal and proximal ends, and a jaw assembly located at the distal end of the elongated body, the jaw assembly configured for cutting a side branch vessel, wherein the jaw assembly has a first jaw, a second jaw, and an electrode secured to the first jaw, wherein the second jaw has a raised portion that faces towards the first jaw, and the electrode has two side electrode portions and a middle electrode portion that is between the two side electrode portions, the raised portion of the second jaw being in alignment with the middle electrode portion. In other embodiments, instead of cutting a side branch vessel, the jaw assembly may be used to cut other tissue, such as tissue at a main branch vessel, etc.

In accordance with other embodiments, a surgical instrument includes an elongated body having a distal end, a proximal end, and a bore extending between the distal and proximal ends, and a jaw assembly located at the distal end of the elongated body, the jaw assembly configured for cutting tissue, wherein the jaw assembly has a first jaw, a second jaw, and an electrode secured to the first jaw, wherein the electrode has two side electrode portions and a middle electrode portion that is between the two side electrode portions, the electrode is planar and extends beyond an edge of the first jaw, and the electrode is insulated by a non-conductive portion of the first jaw.

Other and further aspects and features will be evident from reading the following detailed description of the embodiments, which are intended to illustrate, not limit, the invention.

BRIEF DESCRIPTIONS OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 8 is a partial perspective view of a pair of jaws at a distal end of a surgical instrument, wherein the jaws are being operated as a monopolar electrode in accordance with some embodiments;

FIG. 9A is a partial perspective view of a pair of jaws in accordance with some embodiments;

FIG. 9B shows the device of FIG. 9A, showing that part of the device is covered by an insulative layer;

FIG. 10A is a cross sectional view of the pair of jaws of FIG. 9A in accordance with some embodiments;

DETAILED DESCRIPTION

Figure 1:
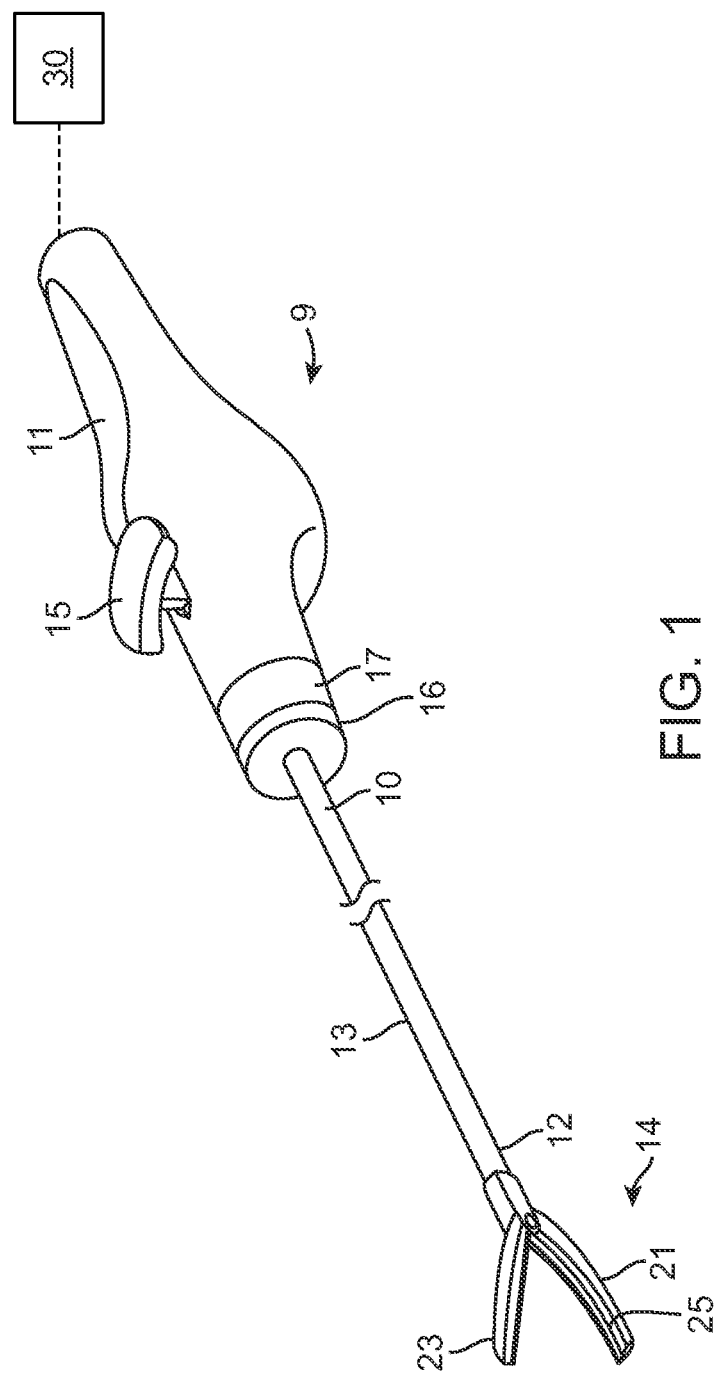
FIG. 1 illustrates a surgical instrument in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a surgical instrument 9 in accordance with some embodiments. The surgical instrument 9 includes a handle 11, an elongated body 13 having a proximal end 10 and a distal end 12, and a surgical device 14 located at the distal end 12 of the body 13. The proximal end 10 of the elongated body 13 is coupled to a distal end 16 of the handle 11. As used in this specification, the term "surgical device" refers to any device or component that may be used to operate on tissue (e.g., to treat, manipulate, handle, hold, cut, heat, or energize, etc., tissue). The elongated body 14 may be rigid, or alternatively, flexible. The handle 11 includes a manual actuator 15 (e.g., a button) that is coupled to the surgical device 14 through linkage (not shown) within a bore of the body 13 for manually controlling an operation of the surgical device 14. The handle 11 and the actuator 15 may be made from insulative material(s) such as plastic.

In the illustrated embodiments, the surgical device 14 includes a pair of jaws 21, 23 for clamping, cutting, and sealing a vessel. The jaw 21 includes an electrically conductive material 25 which faces towards the opposing jaw 23. Alternatively, or additionally, the jaw 23 may include an electrically conductive material which faces towards jaw 21. The electrically conductive material 25 is in a form of an electrode, and is configured to selectively provide heat or RF energy during use. As used in this specification, the term "electrode" refers to a component that is for delivering energy, such as heat energy, RF energy, etc., and thus, should not be limited to a component that delivers any particular form of energy. The electrically conductive material 25 may be Ni-chrome, stainless steel, or other metals or alloys in different embodiments. The jaws 21, 23 are configured to close in response to actuation (e.g., pressing, pulling, or pushing, etc.) of the button 15, thereby clamping a vessel during use. In the illustrated embodiments, the button 15 may be further actuated (e.g., further pressed, further pulled, or further pushed, etc.) to cause the electrically conductive material 25 to provide heat, thereby cutting and sealing the clamped vessel. In particular, when the button is further actuated, the electrically conductive material 25 is electrically coupled to a DC source 30, which provides a current to the electrically conductive material (electrode) 25, thereby heating the electrode 25. After the vessel is cut and sealed, the button 15 may be de-actuated to open the jaws 21, 23, thereby stopping the delivery of heat. The mechanical linkage for translating operation of the button 15 into closing and opening of the jaws 21, 23 may be implemented using cables, shafts, gears, or any of other mechanical devices that are known in the art.

In the illustrated embodiments, the handle 11 also includes an electrical contact region 17 that is in a form of a ring located near the distal end 16 of the handle 11. The contact region 17 is electrically coupled to the electrically conductive material 25 at the surgical device 14, and is configured (e.g., shaped, sized, and positioned) for receiving RF energy from a RF source. In some embodiments, the contact region 17 is electrically connected to the electrode 25 via electrical line that may be housed within a wall of the elongated body 13, or that may be in a form of a cable that is housed within the bore of the elongated body 13. In some embodiments, the elongated body 13 may include an outer layer of bioinert electrically insulative material. In other embodiments, instead of being in a form of a ring, the contact region 17 may be in a form of a small pad or other contact(s) located near the distal end 16 of the handle 11.

The linkage that mechanically couples the jaws 21, 23 to the actuator 15 may be electrically insulated, for example, by silicone rubber, ceramic or other suitable non-electrically conductive material. This assures that high frequency energy supplied to the contact region 17 is conducted along the electric line housed by the body 13 to the electrically conductive material (electrode) 25 at jaw 21 (and/or electrode at jaw 23). In other embodiments, the body 13 may not include an electric line for coupling the contact region 17 to the electrode 25. Instead, the linkage that mechanically couples the jaws 21, 23 to the actuator 15 may be electrically conductive, and is used to couple RF energy received at the contact region 17 to the electrode 25 at jaw 21 (and/or electrode at jaw 23). For example, the linkage may be slidably coupled to the contact region 17.

Figure 2:
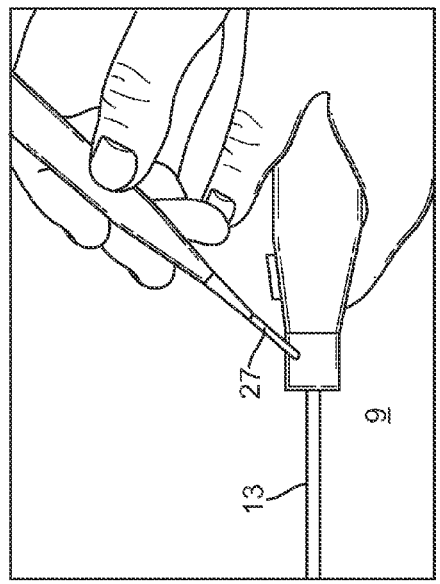
FIGS. 2-4 are partial perspective views of a contact ring on a handle, particularly showing the contact ring being engaged at various angular orientations with an electrode of an RF source of energy to provide cauterization at the distal end of the instrument.
Figure 3:
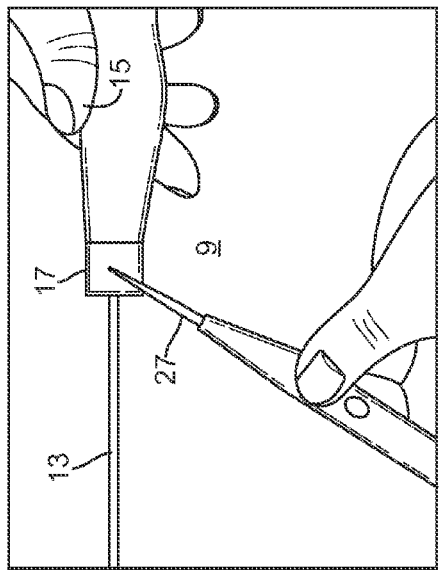
Figure 4:
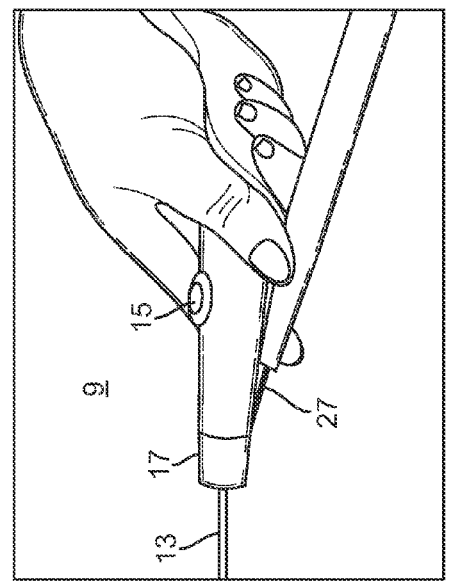

In operation, as illustrated in the partial perspective views of FIGS. 2-4, the contact region 17 on the handle 11 of the surgical instrument 9 is contacted by the electrode 27 of an electrosurgical RF probe (e.g., a conventional BOVIE pencil), which is electrically coupled to a high frequency energy source (e.g., electrosurgical RF generator). The manual contact of the contact region 17 by the electrode 27 may be effected from any convenient angle of the electrosurgical RF probe relative to the longitudinal axis of the body 13, and at any angular orientation of the body 13 (about its longitudinal axis). This is one advantage of using a ring configuration for the contact region 17. As illustrated in the figure, the contact region 17 allows delivering of high frequency energy from the electrosurgical RF generator to the electrosurgical RF probe, and to the electrode 25 of the surgical device 14. A return monopolar RF electrode that may be in a form of a pad (not shown) is coupled to the skin of the patient, and is electrically connected to a terminal of the RF generator. Thus, RF energy is delivered at the electrode 25, and is returned to the RF generator via the return monopolar RF electrode.

Figure 5:
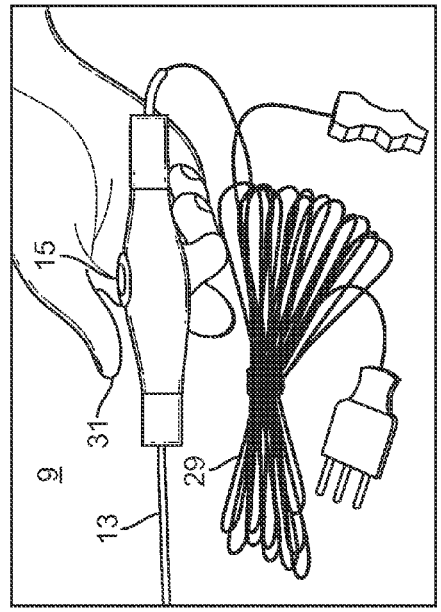
FIG. 5 is a partial perspective view of a surgical instrument that includes a thumb switch for delivering RF energy in accordance with other embodiments.

FIG. 5 illustrates a variation of the surgical instrument 9 in accordance with other embodiments. In the illustrated embodiments, instead of having a contact region that is for contact with the electrosurgical RF probe, the surgical instrument 9 includes an additional button 31 located at the handle 11. The button 31 is thumb-actuated, and is configured to electrically couple the electrically conductive material at the surgical device 14 to a RF source, wherein the RF source is configured to provide high frequency energy to the surgical instrument 9 (i.e., to the electrically conductive material 25 at the surgical device 14) via cable 29. In some embodiments, the surgical instrument 9 provides two modes of operation. In a first mode of operation, when the button 31 is actuated, the electrically conductive material 25 is electrically coupled to the RF source, which supplies RF energy to the electrically conductive material for bleeding control. Also, in the first mode of operation, when the button 31 is actuated, the electrically conductive material 25 is electrically decoupled from the DC source 30 so that current cannot be provided to the electrically conductive material from the DC source 30 for heating the electrically conductive material 25 (e.g., even if the first button 15 is actuated). In a second mode of operation, when the button 31 is de-actuated, the electrically conductive material 25 is electrically coupled to the DC source 30, so that the DC source 30 can supply a current to the electrically conductive material 25 for heating the electrically conductive material 25. In other embodiments, when the button 31 is de-actuated, the electrically conductive material 25 is allowed to be electrically coupled to the DC source 30 by activation of the first button 15.

It should be noted that the term "first mode" does not need to be associated with supplying RF energy, and that the term "second mode" does not need to be associated with supplying heat energy. As used in this specification, the terms "first mode" and "second mode" refer to different modes. Thus, in other embodiments, the first mode of operation may be achieved by supplying heat energy, and the second mode of operation may be achieved by supplying RF energy. Also, it should be noted that the operation of the button 31 may be reversed in other embodiments. In particular, in other embodiments, actuating the button 31 would enable delivery of heat energy (and disallow delivery of RF energy), and de-actuating the button 31 would enable delivery of RF energy (and disallow delivery of heat energy).

Figure 6:
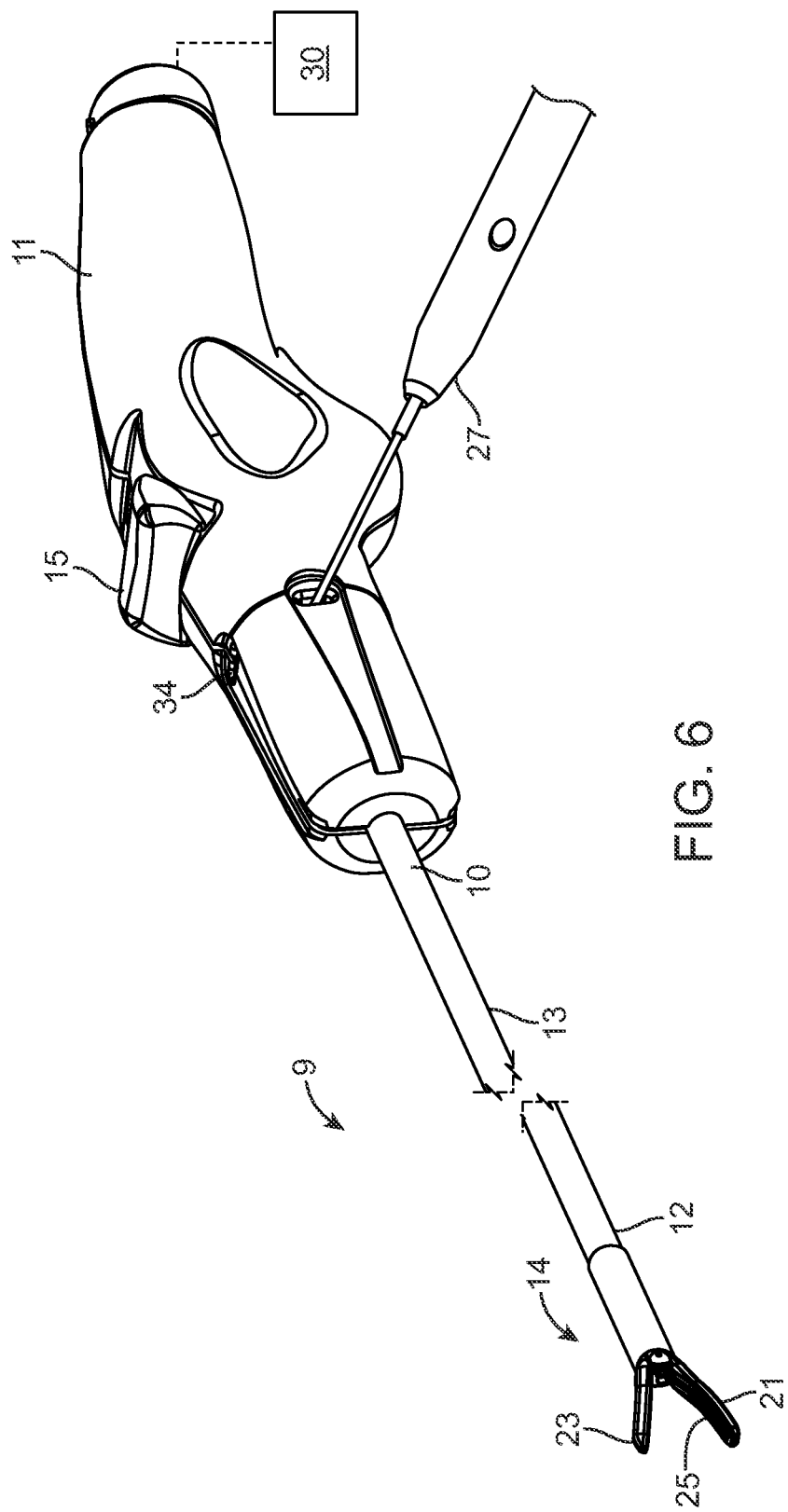
FIGS. 6 and 7 are partial perspective views of another surgical instrument that includes a port for receiving RF energy supplied by another instrument in accordance with some embodiments.
Figure 7:
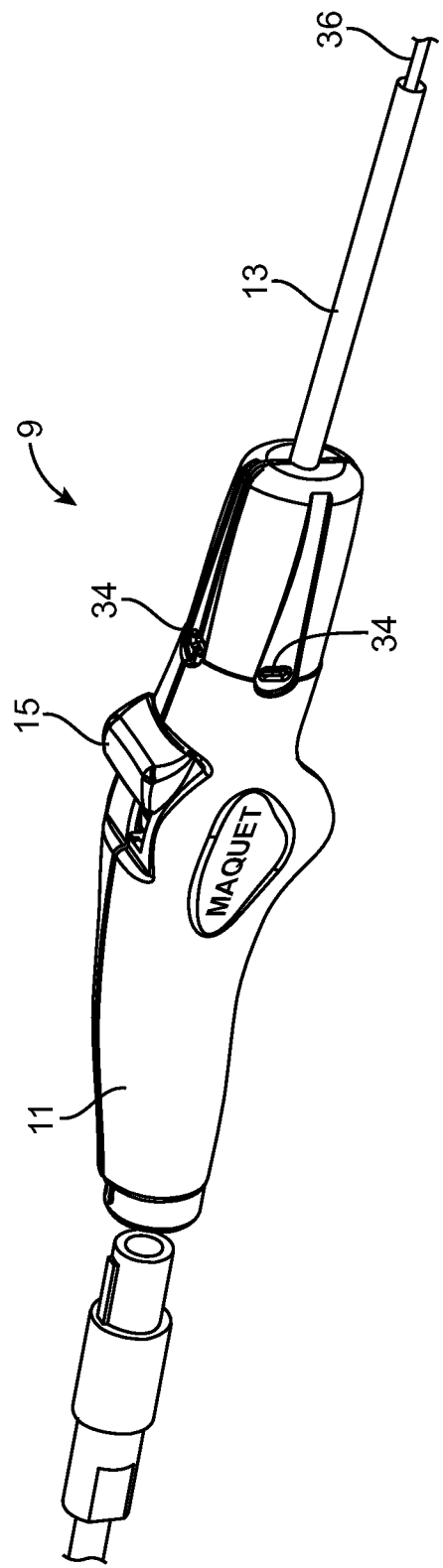

FIGS. 6 and 7 illustrate another variation of the surgical instrument 9 in accordance with other embodiments. In the illustrated embodiments, instead of having a contact region that is in a form of an outer ring at/near the handle 11, the surgical instrument 9 includes one or more connection ports 34 disposed about the periphery of the handle 11 near its distal end 16. Each such connection port 34 includes a contact terminal configured to receive the tip of an electrosurgical RF probe 27, and to electrically connect such probe 27 through the electrical line housed in the body 13 (or through the mechanical linkage, e.g., the actuating rod 36, within the body 13 if the linkage is electrically conductive) to the electrically conductive material 25 at the distal end. If a plurality of ports 34 are provided circumferentially about the distal portion of the handle 11, then the surgical instrument 9 has the advantage of allowing the RF probe 27 to make contact with a terminal no matter how the body 13 is oriented about is longitudinal axis. In the illustrated embodiments, the actuating rod 36 is mechanically linked to the manual actuator 15 in conventional manner to slidably translate within the body 13 in response to fore and aft movements of the manual actuator 15. Translational movement of the rod 36 is linked to the jaws 21, 23 in conventional manner to open and close the jaws in response to movement of the manual actuator 15. As illustrated in the embodiments, providing port(s) 34 and contact terminal(s) in the port(s) 34 is advantageous in that such configuration may prevent unintentional contact of the contact terminal(s) by the patient during use. In other embodiments, instead of providing port(s) 34 at the handle 11, the port(s) 34 may be provided at the body 13.

In the illustrated embodiments, operation of the manual actuator 15 allows selective delivery of heat energy or RF energy in different modes of operation. In some embodiments, activating the manual actuator 15 will result in closing of the jaw assembly. The activating of the manual actuator 15 will also configure an internal switch, which allows a current to be delivered to the conductive material 25 for providing heat, and prevents energy from the RF source from being delivered to the conductive material 25. When the manual actuator 15 is de-activated, the internal switch is configured in a different way, which allows RF energy to be delivered to the conductive material 25, and prevents energy from the DC source from being delivered to the conductive material 25. The internal switch will be described in further details below with reference to FIG. 11B.

FIG. 9A illustrates the pair of jaws 21, 23 in accordance with some embodiments. As shown in the figure, the electrically conductive material 25 forms a heating element (electrode) 40 that is disposed on a surface of the jaw 21. The heater element 40 includes two outer portions 50, 52, and an inner (middle) portion 48. The outer portions 50, 52 have respective outer terminals 44, 46 at their ends, and the middle portion 48 has an inner terminal 42 at its end. Thus, the portions 48, 50, 52 form an electrical heater circuit between the center terminal 42 and outer terminals 44, 46. In the illustrated embodiments, the outer portions 50, 52 and the inner portion 48 function as an electrode that is configured to deliver heat in one mode of operation, and deliver RF energy in another mode of operation. In particular, in one mode of operation, the terminal 42 of the electrode 40 is electrically coupled to a first terminal of the DC source 30, and terminals 44, 46 of the electrode 40 are electrically coupled to a second terminal of the DC source 30, thereby allowing the electrode 40 to receive DC energy (e.g., for cutting and/or welding tissue). In another mode of operation, the electrode 40 is electrically coupled to a RF source for receiving RF energy (e.g., for bleeding control). The heating element 40 may be formed using a single, flat sheet of electrically conductive material (e.g., Ni-chrome alloy, such as stainless steel at an outer layer, and Ni-chrome at an inner layer). This has reliability, manufacturing and cost advantages. It also reduces the likelihood of tissue build up and entrapment during use by not creating crevices into which the tissue can migrate. Optionally, a distal end 41 of the heater element 40 may be disposed beyond the distal end of the jaw 21 (at the distal tip) to serve as an exposed RF monopolar electrode. This allows cauterization of tissue by RF energy to be performed using the distal tip of the jaw 21

As shown in FIG. 9A, the jaw-operating mechanism and linkage thereof to the actuating rod 36 may be supported in a metal housing 68 that includes metal sliding pin 70 and attachment pin 72, all covered with an insulating layer 100 (FIG. 9B) of flexible material such as silicone rubber, or the like, to restrict energy discharges and to isolate tissue from moving parts. Also, such insulating cover retains the sliding and attachment pins 70, 72 in place to obviate the need for more expensive fasteners and mechanisms.

During use, in the first mode of operation, current from the DC source 30 is conducted through the center terminal 42, and flows in the middle portion 48 of the heater element 40 and in parallel through the dual outer portions 50, 52 of the heating element 40 to the common terminals 44, 46. Thus, for heater portions 48, 50, 52 of equal thicknesses and equal widths, current density in the middle portion 48 is twice as high as the current density in each of the outer portions 50, 52 in response to electrical heater signal applied between terminal 42 and the common terminals 44, 46. Of course, current densities in the center and outer portions 48, 50, 52 may be altered (for example, by altering the relative widths of the heater portions, by altering resistances through selection of different materials, by altering both the widths and resistances, etc.) to alter the operating temperatures thereof in response to applied electrical heater signals. In operation, the outer heater portions 50, 52 may operate at a temperature sufficient to weld a tissue structure (e.g., a blood vessel) grasped between the jaws 21, 23, and the center heater portion 48 may operate at a higher temperature sufficient to sever the grasped tissue structure intermediate the welded segments. In the second mode of operation, the heater element 40 does not receive current from the DC source 30. Instead, the heater element 40 operates as a RF electrode (e.g., a monopolar electrode) and delivers RF energy that is provided from the RF generator, and that is transmitted to the heater element 40 via the contact region 17. The application of the RF energy may be used to control bleeding at tissue that is at the surgical site, e.g., tissue that is next to the vessel being harvested, or tissue next to a side branch vessel, etc.

Referring now to FIG. 10A, there is shown a partial cross sectional view of the jaws 21, 23 that illustrates the placement of heater portions 48, 50, 52. The jaw 21 includes a structural support 64, and the jaw 23 includes a structural support 66. In some embodiments, the structural supports 64, 66 may be made from electrically conductive material that allows the supports 64, 66 to function as electrical lines (e.g., for transmitting current, RF signal, etc.). The structural supports 64, 66 are covered by respective layers of electrically insulating material, such as rubber, polymers, silicone, polycarbonate, ceramic or other suitable insulating material. The layers may be molded separately and bonded onto the respective structural supports 64, 66. Alternatively, the layers may be overmolded onto the structural supports 64, 66. As shown in the figure, the jaw 23 includes a surface elevation (protrusion) 54 substantially in alignment with the middle portion 48 in order to increase the compression force applied to a tissue structure grasped by the jaws 21, 23 and in contact with the middle portion 48. This promotes more efficient tissue severance, while adjacent regions 56, 58 of lower surface elevations on jaw 23 in alignment with the outer portions 50, 52 of the heater element introduce less compression force suitable for welding grasped tissue.

Figure 10B:
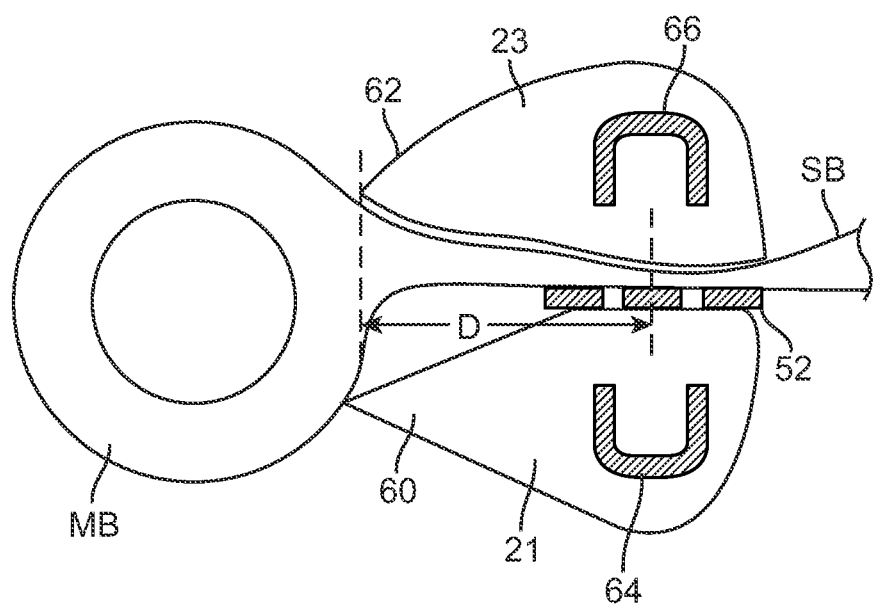
FIG. 10B is a cross sectional view of the pair of jaws of FIG. 9A, showing the jaws being used to cut a side branch vessel.

In the illustrated embodiments, the cross sections of the respective jaws 21, 23 are not symmetrical. Instead, jaw 21 has a protrusion 60, and jaw 23 has a protrusion 62. Each of the protrusions 60, 62 has a length so that when the protrusions 60, 62 abut against a main branch vessel MB, the cutting point of the side branch vessel SB is at a prescribed distance D that is spaced away from the main branch vessel MB (FIG. 10B). In the illustrated embodiments, the distance D is at least 1 mm, and more preferably, at least 1.5 mm. In other embodiments, the distance D may have other values, such as that which is sufficient to prevent or minimize thermal spread from electrode 40 to the main branch vessel MB being harvested. As illustrated in the embodiments, the protrusions 60, 62 are advantageous in that they help reduce thermal spread resulting from the cutting and sealing of the side branch vessel SB, thereby preserving the integrity of the main branch vessel MB that is being harvested. Also, the protrusions 60, 62 obviate the need for an operator to guess whether the cutting of the side branch vessel SB is sufficiently far (e.g., beyond a minimum prescribed spacing) from the main branch vessel MB. Instead, the operator merely abuts the protrusions 60, 62 of the jaw assembly against the main branch vessel MB, and the protrusions 60, 62 will automatically place the jaw assembly relative to the side branch vessel SB so that the side branch vessel SB is cut at a minimum prescribed distance D from the main branch vessel MB. In some cases, if the surgical instrument 9 is used to cut other types of tissue, such as nerves, organs, tendons, etc., the protrusions 60, 62 also provide the same benefits of preserving the integrity of tissue that is being cut, and obviating the need for a user to guess what is the appropriate margin. As shown in the figure, the protrusions 60, 62 diverge away from part of the side branch vessel SB. Such configuration allows part of the side branch vessel SB that is immediately next to the main branch vessel MB not to be clamped by the jaws. As a result, the end of the side branch vessel SB will fall away once it is cut. In other embodiments, the surgical instrument 9 does not need to include both protrusions 60, 62. Instead, the surgical instrument 9 may include either protrusion 60 or protrusion 62. Such configuration allows the device at the distal end of the instrument 9 to have a smaller profile, thereby allowing a user to effectively maneuver the distal device in tight tissue conditions. As shown in the figure, the heater portion 52 may protrude laterally along an outer edge of the closed jaws 21, 23 to serve as an RF electrode on RF signal applied thereto in a manner described herein, while the heater portion 50 is shrouded or recessed within the lateral protrusions 60, 62 on the jaws 21, 23 for more controlled emission of applied RF signal from along mainly (or only) the exposed edge of the heater portion 52.

As shown in FIG. 8, the jaw assembly has a concave side and a convex side. In one method of use, while the jaw assembly is used to cut a side branch vessel SB, the jaw assembly is oriented so that its concave side faces towards the main branch vessel MB. The endoscope or viewing device may be placed next to the jaw assembly with the endoscope or viewing device viewing the concave side of the jaw assembly. This allows the user to better visualize the tip of the jaw assembly. Such configuration also provides a safety feature by allowing the user to know where the tips are during the vessel cutting procedure. Also as shown in FIG. 8, the exposed electrode portion 52 is on the convex side of the jaw assembly while the protrusions 60, 62 are on the concave side of the jaw assembly. The concavity provides extra spacing to protect the main branch vessel MB by keeping the distance along the side branch vessel SB even greater when it is grasped. Furthermore, having the exposed electrode 52 on the convex side creates an apex point that makes it easier to contact the side wall of the tunnel to address bleeding. In other embodiments, the protrusions 60, 62 may be on the convex side of the jaw assembly. In such cases, during use, the convex side of the jaw assembly would be oriented towards the main branch vessel MB, thereby ensuring that the tips of the jaw assembly are away from the main branch vessel MB to enhance protection (e.g., preventing the tip of the jaw assembly from touching or injuring the main branch vessel MB).

Figure 11A:
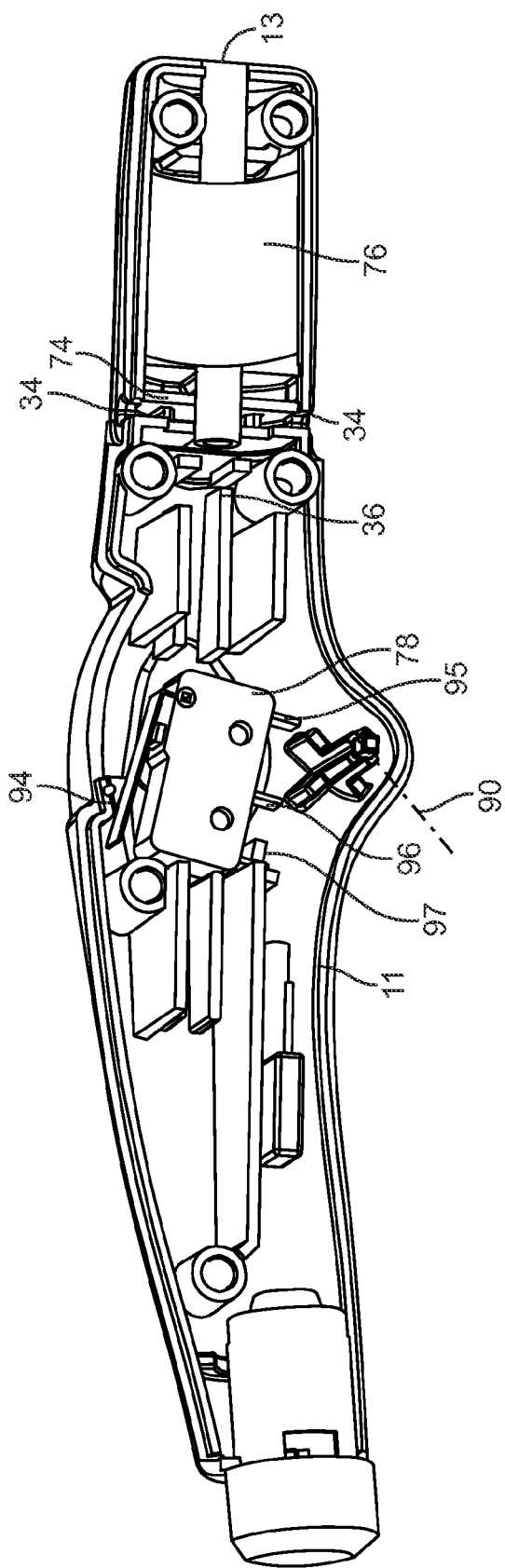
FIGS. 11a and 11B are partial views of a handle showing its internal operational mechanisms at a proximal end of a surgical instrument in accordance with some embodiments.
Figure 11B:
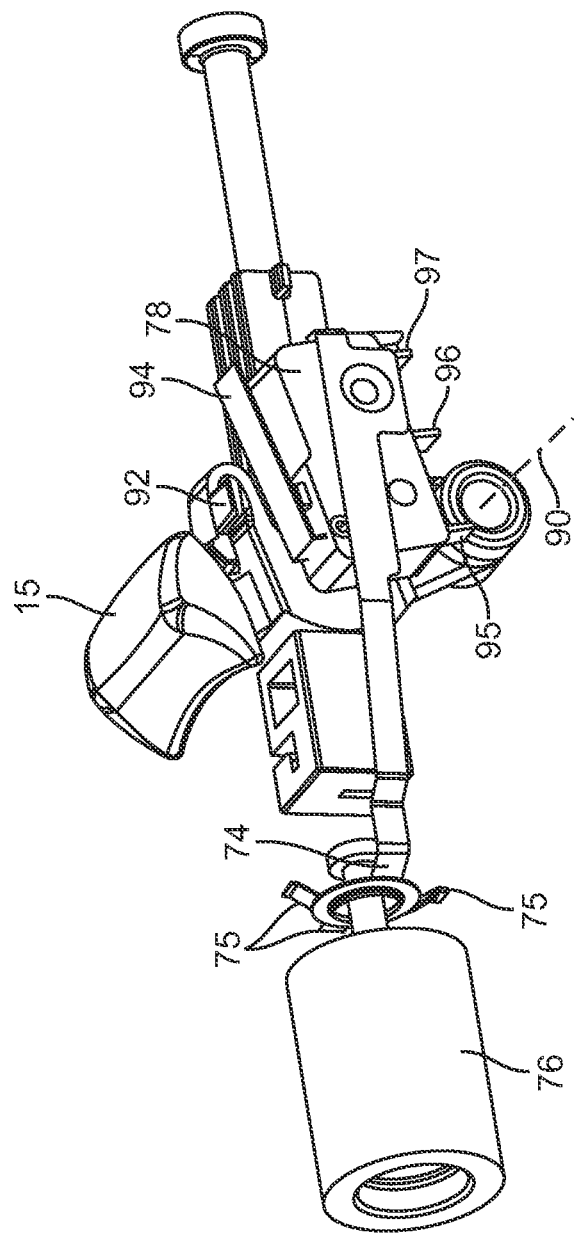

Referring now to the partial cutaway view of FIG. 11A and the partial view of FIG. 11B, which shows interior components of the handle 11. A resilient electrical contacting device 74 is disposed within the handle 11. The contacting device 74 includes a plurality of resilient contact terminals 75 (each of which may be considered a contact region) that are aligned with respective connection ports 34. Each port 34 allows access by a RF probe, such as a conventional BOVIE pencil, to make contact with the corresponding contact terminal 75 therein, as illustrated in FIG. 6. A smoke filter 76 is positioned in the forward end of the handle 11. The filter 76 is for filtering steam/smoke generated during operation of the device (e.g., steam/smoke resulted from cutting tissue, welding tissue, and/or bleeding control) so that the steam/smoke would not interfere with the user of the surgical instrument 9, and help improve visualization in the working site. During use, the working tunnel has a pressure differential caused by pressurized gas (e.g., $CO_2$) such the smoke is forced out of the tunnel, into the device tip, down the shaft, and into the filter 76 of the handle 11. The actuator rod 36 is mechanically linked in conventional manner to the manual actuator 38 (not shown in the figure for clarity) to slidably translate the rod 36 within the outer body 13 for remotely operating the jaws 21, 23 between open and closed positions. An electrical switch 78 is mounted in the handle 11 to be operated in conjunction with the manual actuator 38 for controlling electrical power supplied to the heater element 48, 50, 52. In particular, the actuator 38 has a portion 92 for engagement with a lever 94 of the switch 78. The switch 78 has a first contact (common contact) 95, a second contact (normally-open contact) 96, and a third contact (normally-closed contact) 97. The first contact 95 is electrically connected to a terminal of the heating element (electrode) 40 (e.g., via a wire), and the second contact 96 is electrically connected to a first terminal of the DC source 30. Another terminal of the heating element (electrode) 40 is electrically connected to a second terminal of the DC source 30 (e.g., via a wire). As shown in FIG. 11B, the contact 74 is electrically connected to the third contact 97 of the electric switch 78. Electrical switches that may be used with the handle 11 are commercially available from E-Switch, at Brooklyn Park, Minn. The handle assembly 11 is completed with a complementary half section (not shown) that snaps together with, or is otherwise attached to the illustrated half section. The handle 11 is formed of plastic material that also provides electrical insulation from RF emissions while the device 9 is connected with the RF generator in the manner as previously describe herein. In some cases, the material for construction of the handle 11 is selected so that it provides adequate strength for the handle 11 to withstand forces of the mechanisms and forces of the user interacting with the device during a procedure.

During use, when the actuator 38 is pushed forward (by rotating about axis 90) to push rod 36, the translation motion of the rod 36 causes the jaws 21, 23 to open. The opened jaws 21, 23 can then be used to grasp tissue (e.g., side branch vessel). When the jaws 21, 23 are placed around target tissue, the actuator 38 may be pulled backward to pull rod 36. The translation motion of the rod 36 causes the jaws 21, 23 to close, thereby gripping the target tissue. If desired, the actuator 38 may be further pulled backward to cause the portion 92 of the actuator 38 to engage the lever 94 of the electrical switch 78. This in turn causes the first contact 95 to be electrically connected to the second contact 96 within the switch 78, thereby supplying DC power from the DC source to the heater element (electrode) 40. Inside the switch 78, when the second contact 96 is electrically connected to the first contact 95, the third contact 97 is electrically de-coupled from the first contact 95. Thus, while DC energy is being delivered to the electrode 40 (e.g., for providing heat to cut and/or weld tissue), the contact 74 will not be able to transmit RF energy (e.g., from an electrosurgical RF probe) to the electrode 40. The delivery of DC energy may be stopped by pushing the actuator 38 forward so that the portion 92 is disengaged from the lever 94. When this happens, the second contact 96 is electrically disconnected from the first contact 95 inside the switch 78, and the third contact 97 is electrically connected to the first contact 95 inside the switch 78. Such configuration allows RF energy (from the electrosurgical RF probe delivered at the contact 74 and transmitted to the third contact 97) to be transmitted to the electrode 40 (e.g., for bleeding control). Note that in this mode of operation, DC energy cannot be delivered to the electrode 40 because the first and second contacts of the switch 78 is not electrically connected.

Figure 12:
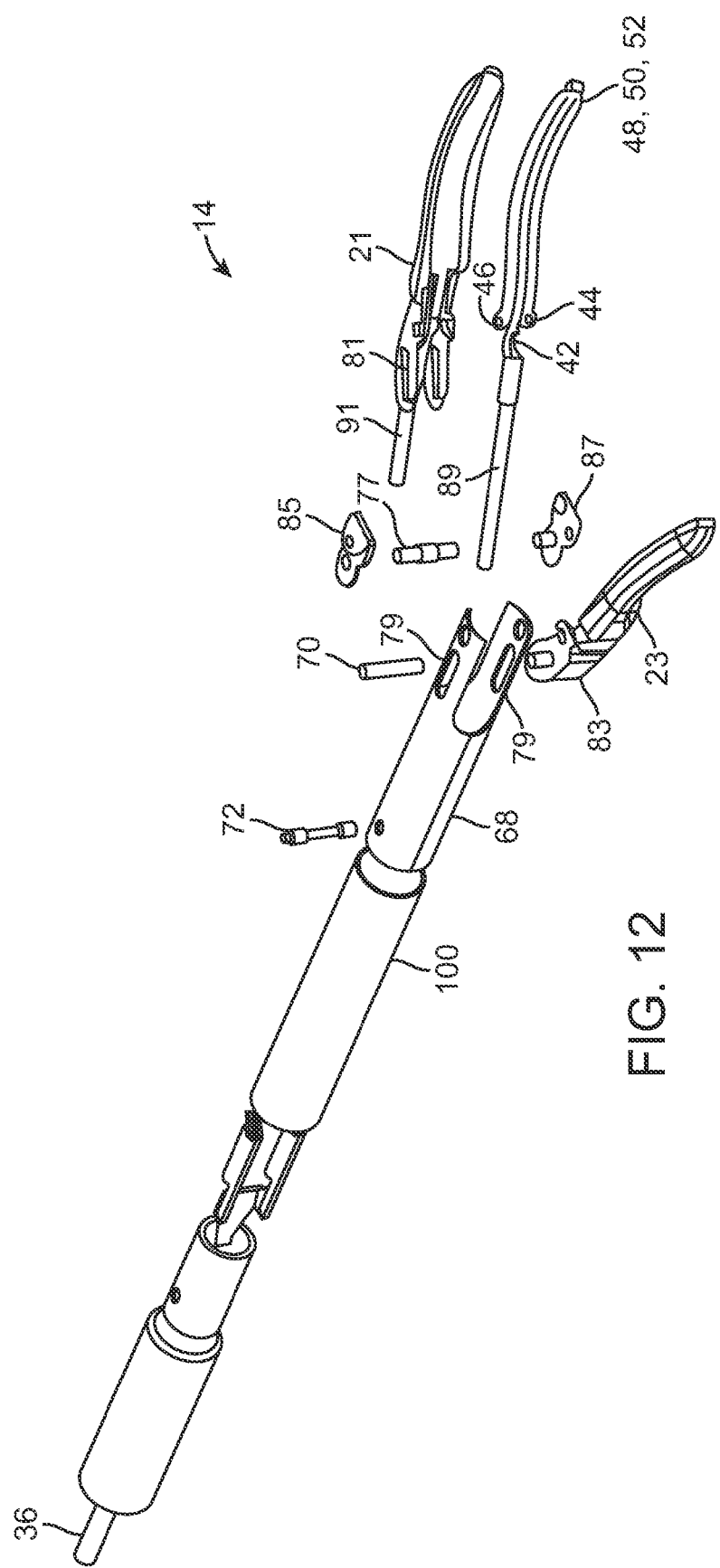
FIG. 12 is a partial exploded view of the components of a surgical instrument in accordance with some embodiments.

Referring now to FIG. 12, there is illustrated an exploded view of the components forming the surgical device 14, and its attachment to the distal end of the body 13. Specifically, the heater elements 48, 50, 52 (conductive material 25) are attached to jaw 21. Both jaws 21, 23 are pivotally attached via pin 77 to the metal housing 68. Pin 70 is disposed to slide within the aligned slots 79, and within the mating angled slots 81, 83 in the frame-mounts of the associated jaws to effect scissor-like jaw movement between open and closed positions as the slide pin 70 is moved relative to the pivot pin 77. Actuator rod 36 is linked to the slide pin 70, for example, via mating elements 85, 87. Axial movement of the rod 36 in one direction will cause the slide pin 70 to move towards the pin 77, thereby opening the jaws 21, 23. Axial movement of the rod 36 in the opposite direction will cause the slide pin 70 to move away from the pin 77, thereby closing the jaws 21, 23. An electrical conductor 89 connects to the inner terminal 42 of the heating element 48, 50, 52, and the outer terminals 44, 46 are electrically connected in common to conductor 91. In some embodiments, either conductor 89 or 91 may be housed within the wall or the bore of the elongated body 13. In other embodiments, if the rod 36 is electrically conductive, either conductor 89 or 91 may be coupled to the rod 36. In such cases, the rod 36 will be electrically coupled to one terminal of the DC source 30, or to the contact 95 of the switch 78, during use. During use, the conductors 89, 91 may be electrically coupled to terminals of the DC source 30, which provides a current to thereby heat up the heater elements 48, 50, 52. The center heater element 48 is configured to cut a vessel (e.g., a side branch vessel) while the outer heater elements 50, 52 are configured to weld (seal) the vessel. In some embodiments, parts of the surgical device 14 may be insulated via an outer insulating layer for restricting RF emissions (when the bleeding control function is used) and for isolating certain components from biologic tissue and fluids. In the illustrated embodiments, the surgical instrument 9 includes an insulative cover 100.

During use of the surgical instrument 9, the body 13 is advanced along a vessel to be harvested. In some cases, the instrument 9 may be placed into an instrument channel of a cannula, which includes a viewing device, such as an endoscope, for allowing an operator to see the distal end of the instrument 9 inside the patient. When a side branch vessel (or other target tissue) is encountered, the jaws 21, 23 may be used to grasp and compress the side-branch vessel in response to manual manipulation of the actuator 38. Power is then supplied using the DC source 30 to the heater elements 48, 50, 52 (which function as resistive element that heats up in response to the delivered direct current) to effect tissue welds at tissues that are in contact with outer segments 50, 52, and to effect tissue cutting at tissue that is in contact with segment 48.

During the vessel harvesting procedure, if the operator notices that there is bleeding next to the vessel being harvested (e.g., at peripheral vasculature), the operator may position the electrosurgical RF probe 27 so that it is in contact with the contact region 17/74 at the handle 11. This results in RF energy being supplied (or allowed to be supplied) from the attached electrosurgical RF generator. In some cases, a foot-actuated switch may be provided that allows the operator to direct RF energy from the RF generator to the RF probe 27. The supplied RF energy from the RF generator is conducted to the electrically conductive material 25 at the distal surgical device 14, and the energy is returned via a return electrode pad that is coupled to a skin of the patient. The electrically conductive material 25 serves as a monopole RF electrode to electrocauterize any tissue (e.g., vessel tissue or surrounding tissue) that is grasped between the jaws 21, 23. Alternatively, the lateral edge of the heater element 52 that protrudes from a side of the jaw 21 may be used to cauterize bleeding area. In such cases, the jaws 21, 23 may or may not be closed, and may or may not be grasping any tissue. For example, in some embodiments, the operator may not be using the jaws 21, 23 to grasp or cut tissue. However, if the operator notices that there is bleeding at or near the surgical site, the operator may use the element 52 protruding from a side of the jaw 21 to cauterize the bleeding area (e.g., such as that shown in FIG. 8). In particular, the element 52 serves as an RF monopole electrode for electrocauterizing the tissue.

In some embodiments, the exposed portion of the element 52 may also be used as a DC electrode for controlling bleeding. For example, the side or the tip of the element 52 that extends beyond the profile of the jaw assembly may be used to perform thermal spot cauterization by direct thermal conduction. In such cases, the element 52 may be heated up, and its exposed edge (or tip) may be used to touch tissue that is desired to be cauterized.

Figure 13:
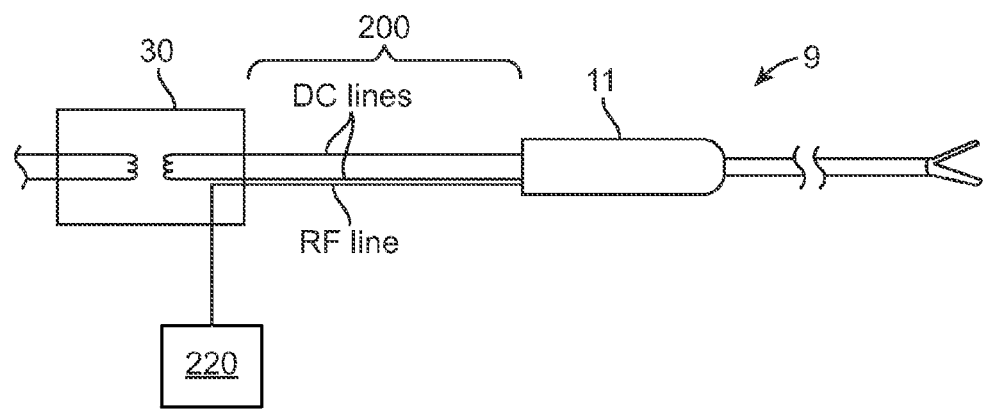
FIG. 13 illustrates a surgical instrument coupled to a DC source and a RF source in accordance with other embodiments.

In the above embodiments, the surgical instrument 9 has been described as having contact region(s) for allowing a RF probe to make contact, thereby causing the surgical instrument 9 to deliver RF energy at its distal end. However, in other embodiments, the surgical instrument 9 may be configured to deliver RF energy without using any RF probe to make contact with it. For example, in other embodiments, the surgical instrument 9 may be coupled to the DC source 30 via a cable 200, wherein the cable 200 is for delivering DC energy from the DC source 30 to the surgical instrument 9 (FIG. 13). The cable 200 also includes circuitry for receiving RF energy from a RF source 220 that is coupled to the DC source, as shown in the figure. In one mode of operation, the DC source 30 is configured to transmit DC energy to the surgical instrument 9. In another mode of operation, the DC source 30 is configured to allow RF source 220 to transmit RF energy to the surgical instrument 9. The DC source 30 may include a switch for switching between two modes of operation. Alternatively, the switch may be implemented at any point along the length of the cable 200 or at the handle 11. In some cases, a RF control, such as a button, a foot pedal, etc., may be provided, for allowing a user to direct RF energy to the surgical instrument 9. In such cases, after the mode-switch control is activated for allowing delivery of RF energy, RF energy will not be delivered unless the RF control is actuated by the user. This provides a safety feature for preventing accidental delivery of RF energy from the RF source 220. The RF control may be coupled to the RF source 220, to the DC source 30, or at any point along the RF line. In other embodiments, the RF control may also be implemented as a component at the RF source 220, at the DC source 30, or at the cable 200.

Figure 14:
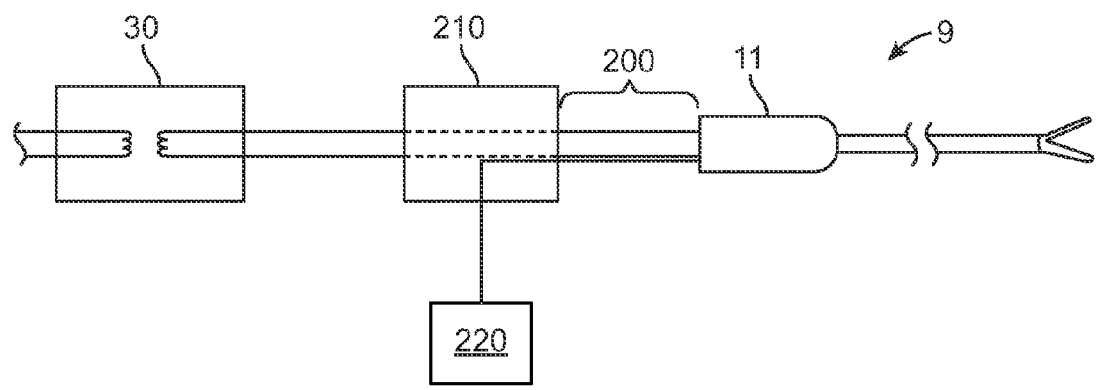
FIG. 14 illustrates a surgical instrument coupled to a DC source and a RF source in accordance with other embodiments.

In other embodiments, the cable 200 may be coupled to a switch box 210. The switch box 210 is configured to receive energy from the DC source 30 and transmit it to the surgical instrument 9 in one mode of operation (FIG. 14). In another mode of operation, the switch box 210 is configured to receive RF energy from a RF source 220, and transmit the RF energy to the surgical instrument 9. The switch box 210 may include a control for allowing a user to switch between the first and second modes of operation. Alternatively, the control for switching between modes of operation may be implemented at any point along the length of the cable 200 or at the handle 11. In some cases, a RF control, such as a button, a foot pedal, etc., may be provided, for allowing a user to direct RF energy to the surgical instrument 9. In such cases, after the switch box 210 is configured to deliver RF energy, RF energy will not be delivered unless the RF control is actuated by the user. This provides a safety feature for preventing accidental delivery of RF energy from the RF source 220. The RF control may be coupled to the RF source 220, the switch box 210, or to any point along the length of the cable 200. In other embodiments, the RF control may also be implemented as a component at the RF source 220, at the switch box 210, or at the cable 200.

As illustrated in the above embodiments, the surgical instrument 9 allows delivering of heat to a remote surgical site for welding and severing vessel, and allows delivering of RF energy for cauterizing tissue to control bleeding. Such instrument is advantageous since combining heat delivery function with RF delivery function would allow a user to address two very different situations (e.g., tissue welding and bleeding control) using a single tool. Also, because many of the components in the instrument 9 that are for providing DC heating are also used for delivering RF energy, the instrument 9 maintains a low profile without any substantial increase in its size. Furthermore, the instrument 9 allows delivery of RF energy in a controlled manner, thereby protecting the vessel being harvested while allowing bleeding to be controlled. Embodiments of the instrument 9 is also advantageous in that it obviates the need for repeatedly inserting a separate bleeding control device inside the patient to control bleeding, and removing such bleeding control device from the patient, during a vessel harvesting procedure. Thus, embodiments of the surgical instrument 9 described herein allows delivery of RF energy in a way that makes it much easier to address bleeding.

Although the above embodiments have been described with reference to the surgical device 14 being a pair of jaws for clamping, cutting, and sealing vessel (e.g., saphenous vein, an artery, or any other vessel), in other embodiments, the surgical device 14 may have different configurations, and different functionalities. For example, in other embodiments, the surgical device 14 may be clip appliers or grasping jaws with no heating functionality, but still include one or more high frequency electrodes for delivering RF energy from RF source to control bleeding. In further embodiments, the bleeding control feature (e.g., the components for allowing RF to be delivered to the distal end of the surgical instrument) may be incorporated in any type of laparoscopic/endoscopic surgical tool. Also, in any of the embodiments described herein, the surgical instrument 9 may be used in any endoscopic procedure that requires transection of tissue with bleeding control.

In addition, although the above embodiments have been described with reference to delivering heat energy and RF energy in different times, in other embodiments, the surgical instrument 9 may be configured to deliver heat energy and RF energy simultaneously. For example, in other embodiments, the surgical instrument 9 may include an electrode for delivering heat energy to cut and/or seal tissue, and another electrode for delivering RF energy for bleeding control. In other embodiments, the surgical instrument 9 may include an operative element for simultaneously delivering heat and RF energy.

Also, although the above embodiments have been described with reference to a surgical instrument that has a bleeding control feature, in other embodiments, such bleeding control feature is optional. Thus, in any of the embodiments described herein, the surgical instrument 9 may not include the port(s) 34, the contact region 17/contact device 74, and the electrical switch 78. In addition, in any of the embodiments described herein, the jaw assembly at the distal end of the surgical instrument 9 does not need to include all of the features described herein. For example, in some embodiments, the jaw assembly does not include outer electrode portions 50, 52. Instead, the jaw assembly includes one electrode strip (like the middle electrode portion 48 described above) for cutting or sealing tissue. Furthermore, in other embodiments, the jaw 23 may not have the raised portion 54. Instead, the jaw 23 may have a flat surface that is for contacting the electrode portions 48, 50, 52. In addition, in further embodiments, the jaws 21, 23 may not include the respective protrusions 60, 62. Instead, the cross section of the jaw 21/23 may have a symmetrical configuration. In other embodiments, protrusion(s) may be provided on both sides of the jaw assembly (e.g., one or more protrusions at the concave side of the jaw assembly, and one or more protrusions at the convex side of the jaw assembly). Such configuration provides buffering on both sides of the jaw assembly, and allows for correct placement of the jaw assembly regardless of which side (the concave or convex side) of the jaw assembly is oriented towards the main branch vessel MB during use. In further embodiments, instead of the curved configuration, the jaws could be straight. Also, in any of the embodiments described herein, instead of, or in addition to, using the electrode 40 for controlling bleeding, the electrode 40 may be used for dissection or transection of tissue, such as fatty and connective tissue encountered during a vessel harvesting procedure.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed is:

1. A surgical instrument comprising:
   an elongated body having a distal end, a proximal end, and a bore extending between the distal and proximal ends, an external surface of the elongated body comprising an electrically insulative material;
   a surgical device including a tissue contact region comprising electrically conductive material, the surgical device is mounted on the distal end of the body;
   a handle coupled to the proximal end of the elongated body, the handle including a proximal end, a distal end, and a manual control moveably mounted thereon, the handle comprising a housing;
   a linkage disposed within the bore, wherein the linkage couples the manual control to the surgical device, and is configured for actuating movement of the surgical device in response to manipulation of the manual control; and
   a contact region of electrically conductive material disposed at the handle and physically accessible to a distal electrode region of a hand-held energy delivery device at a location away from the manual control and on the housing, wherein the contact region is electrically connected to the surgical device and capable of establishing electrical conductivity with the electrically conductive material of the tissue contact region through an electrically conductive path passing at least partially within a region internal to the external surface of the elongated body;
   wherein in a first mode of operation, the electrically conductive material of the tissue contact region of the surgical device is configured to provide heat, and in a second mode of operation, the electrically conductive material of the tissue contact region of the surgical device is configured to provide RF energy when RF energy is directly applied to the contact region via the distal electrode region of the hand-held energy delivery device.

2. The surgical instrument of claim 1, wherein the electrically insulative material of the external surface of the elongated body extends between the distal and proximal ends of the elongated body.

3. The surgical instrument of claim 1, wherein the linkage is electrically conductive.

4. The surgical instrument of claim 1, wherein the elongated body is flexible.

5. The surgical instrument of claim 1, wherein the surgical device includes a pair of jaws that are configured for relative movement between an open position and a closed position.

6. The surgical instrument of claim 5, wherein the pair of jaws is configured to sever tissue.

7. The surgical instrument of claim 6, wherein the tissue comprises vessel tissue.

8. The surgical instrument of claim 5, wherein the electrically conductive material of the tissue contact region is configured for providing the heat in response to an applied current.

9. The surgical instrument of claim 1, wherein the handle includes an opening for allowing access to the contact region by the distal electrode region of the hand-held energy delivery device, wherein the opening is at a location remote from the manual control.

10. The surgical instrument of claim 1, wherein the contact region is in a form of a conductive ring.

11. The surgical instrument of claim 1, wherein the contact region includes a connector within the handle that is accessible through a connection port at the handle.

12. The surgical instrument of claim 1, wherein the contact region is located on an external surface of the handle's housing at a location proximal to the elongated body.

13. The surgical instrument of claim 1, wherein the contact region is configured as a port.

14. A surgical instrument comprising:
an elongated body having a distal end, a proximal end, and a sidewall extending between the distal and proximal ends, an external surface of the sidewall comprised of an electrically insulative material;
a pair of jaws for severing a vessel, the pair of jaws mounted on the distal end of the body, wherein at least one of the jaws has an electrically conductive material;
a handle having a distal end and a proximal end, and coupled to the proximal end of the elongated body, the handle encasing a housing interior cavity;
a contact region located at the handle at a location distal to the handle's proximal end and external to the housing interior cavity, the contact region configured for establishing direct physical contact with a distal electrode tip region of a hand-held energy delivery device;
wherein in a first mode of operation, the electrically conductive material is for receiving energy from a first energy source through a wired connection with the first energy source, and in a second mode of operation, the electrically conductive material is for receiving energy from a second energy source supplied by the hand-held energy delivery device when the distal electrode tip region of the hand-held energy delivery device is in direct physical contact with the contact region.

15. The surgical instrument of claim 14, further comprising a button at the handle, wherein in the first mode of operation, the button is configured for electrically connecting the electrically conductive material to the first energy source, and preventing the electrically conductive material from electrically connecting to the second energy source.

16. The surgical instrument of claim 15, wherein in the second mode of operation, the button is configured for preventing the electrically conductive material from electrically connecting to the first energy source.

17. The surgical instrument of claim 14, wherein the electrically conductive material is configured for providing heat in response to an applied current from the first energy source.

18. The surgical instrument of claim 14, wherein the electrically conductive material is configured for providing RF energy in response to the contact region at the handle being in contact with the distal tip region of the hand-held energy delivery device.

19. The surgical instrument of claim 18, wherein the contact region is recessed within an external surface of the handle for allowing access to the contact region by the hand-held energy delivery device.

20. The surgical instrument of claim 18, wherein the contact region extends in a circumferential direction to be accessible to the hand-held energy delivery device from multiple sides of the surgical instrument.

21. The surgical instrument of claim 14, wherein the handle further includes a button for electrically connecting the contact region to a RF source.

22. The surgical instrument of claim 21, wherein the handle further includes an additional button for closing the jaws and for activating the electrically conductive material to deliver heat.

23. The surgical instrument of claim 14, wherein the electrically conductive material is a part of a heating element disposed on a jaw-facing surface of one of the jaws.

24. The surgical instrument of claim 23, wherein one edge of the heating element is exposed along a longitudinal edge of one of the jaws when the jaws are in a closed configuration.

25. The surgical instrument of claim 14, wherein the contact region is located on an external surface of the handle proximal to the elongated body.

26. A surgical instrument useful for cutting and sealing tissues of a vessel system wherein the vessel system comprises one or more side-branch vessel portions extending from a main-branch vessel portion, the surgical instrument comprising:
an elongated body having a distal end, a proximal end, an axis, and a bore extending between the distal and proximal ends; and
a jaw assembly located at the distal end of the elongated body, wherein the jaw assembly has a first jaw and a second jaw configured to be brought into approximation to each other, the jaw assembly having an electrode secured to the first jaw for cutting a target tissue of the vessel system when such target tissue is located in a first region between the first and second jaw, each jaw of the jaw assembly having a distal end region, a proximal end region, and jaw body located therebetween;
wherein at least one jaw of the jaw assembly has a laterally extending non-conductive protrusion extending from the jaw body in a direction generally perpendicular to the axis and towards a location laterally spaced from the first region, wherein the laterally extending protrusion is sized and shaped so that when the protrusion is abutted against the main-branch vessel portion at a location different than the first region, the electrode is automatically placed at a desired position of the one or more side-branch vessel portions relative to the main-branch vessel portion, and wherein the laterally extending protrusion extends lengthwise along at least a substantial length portion of the jaw body.

27. The surgical instrument of claim 26, wherein the jaw assembly further comprises a component for providing cautery energy.

28. The surgical instrument of claim 27, wherein the component is configured for delivering heat in a first mode of operation, and RF energy in a second mode of operation.

29. The surgical instrument of claim 26, wherein the jaw assembly has a concave side and a convex side.

30. The surgical instrument of claim 29, wherein the protrusion is located at the concave side of the jaw assembly.

31. The surgical instrument of claim 30, further comprising an additional protrusion located at the convex side of the jaw assembly.

32. The surgical instrument of claim 29, wherein the jaw assembly further includes a second electrode at the convex side of the jaw assembly.

33. The surgical instrument of claim 26, wherein the protrusion is for abutment against the main branch vessel portion.

34. The surgical instrument of claim 26, wherein the electrode has an edge that protrudes from a side of the first jaw.

35. The surgical instrument of claim 26, wherein the second jaw has a raised portion that faces towards the first jaw.

36. The surgical instrument of claim 35, wherein the electrode has two side electrode portions and a middle electrode portion that is between the two side electrode portions, and the raised portion of the second jaw is in alignment with the middle electrode portion.

37. The surgical instrument of claim 26, wherein the laterally extending protrusion extends lengthwise along the entire length of the jaw body.

38. A surgical instrument adapted to electrically couple to a DC energy source, the surgical instrument comprising: an elongated body having a distal end, a proximal end, and a bore extending between the distal and proximal ends; and a jaw assembly located at the distal end of the elongated body, the jaw assembly configured for cutting a side branch vessel, wherein the jaw assembly has a first jaw, a second jaw, and an electrode secured to the first jaw; wherein the second jaw has a raised portion and at least one adjacent portion, the adjacent portion is of a different elevation than the raised portion and arranged generally adjacent to the raised portion, wherein both the raised portion and the adjacent portion face towards the first jaw, and the electrode has two side electrode portions and a middle electrode portion that is between the two side electrode portions, the raised portion of the second jaw and the adjacent portion each extend predominantly both distally and proximally lengthwise along the second jaw, wherein the raised portion is in alignment with the middle electrode portion and the adjacent portion is in alignment with one of the two side electrode portions when the first jaw and second jaw are brought into approximation, and wherein at least one jaw of the jaw assembly has a laterally extending non-conductive protrusion extending from a body portion of the jaw in a direction generally perpendicular to a longitudinal axis of the elongated body.

39. A surgical instrument adapted to electrically couple to a DC energy source, the surgical instrument comprising: an elongated body having a distal end, a proximal end, and a bore extending between the distal and proximal ends; and a jaw assembly located at the distal end of the elongated body, the jaw assembly configured for cutting tissue, wherein the jaw assembly has a first jaw, a second jaw, and an electrode secured to the first jaw; wherein the electrode has two side electrode portions and a middle electrode portion that is between the two side electrode portions, the electrode is generally planar and top surfaces of the middle electrode portion and side electrode portion that face the second jaw are generally flat; wherein at least one of the two side electrode portions has a quadrilateral cross-sectional profile and extends along a length of and laterally beyond an edge of the first jaw, the edge extending between a proximal end and a distal end of the first jaw; wherein the surgical instrument is configured such that the electrode is electrically coupled to receive direct current energy from the DC energy source and heat up in response to receiving direct current energy; and wherein the electrode is insulated by a non-conductive portion of the first jaw.

* * * * *